US008985659B2

(12) United States Patent
Kovarik et al.

(10) Patent No.: US 8,985,659 B2
(45) Date of Patent: *Mar. 24, 2015

(54) FISH NETTING TOOL

(71) Applicants: Carter J. Kovarik, Englewood, CO (US); Joseph E. Kovarik, Englewood, CO (US)

(72) Inventors: Carter J. Kovarik, Englewood, CO (US); Joseph E. Kovarik, Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,207

(22) Filed: May 29, 2014

(65) Prior Publication Data

US 2014/0290116 A1   Oct. 2, 2014

Related U.S. Application Data

(63) Continuation-in-part of application No. 14/163,521, filed on Jan. 24, 2014, now Pat. No. 8,833,817, which is a continuation-in-part of application No. 14/078,830, filed on Nov. 13, 2013, now Pat. No. 8,807,615, which is a continuation-in-part of application No. 13/771,813, filed on Feb. 20, 2013, now Pat. No. 8,585,114, application No. 14/290,207, which is a continuation-in-part of application No. 29/462,798, filed on Aug. 8, 2013.

(60) Provisional application No. 61/601,789, filed on Feb. 22, 2012.

(51) Int. Cl.
*A01K 77/00* (2006.01)
*B25J 1/02* (2006.01)
*E01H 1/12* (2006.01)
*A01K 15/00* (2006.01)
*A01K 63/00* (2006.01)

(52) U.S. Cl.
CPC . *A01K 77/00* (2013.01); *B25J 1/02* (2013.01); *E01H 1/1206* (2013.01); *A01K 15/003* (2013.01); *A01K 63/006* (2013.01); *E01H 2001/1273* (2013.01)
USPC ............... 294/209; 294/210; 294/111; 43/11

(58) Field of Classification Search
USPC ......... 294/1.4, 19.2, 111, 115, 190, 209, 210; 81/177.6; 606/205; 43/7, 8, 11, 12, 134
See application file for complete search history.

(56) References Cited

U.S. PATENT DOCUMENTS 388,776 A    8/1888    Hall
826,160 A    7/1906    Hall
(Continued)

FOREIGN PATENT DOCUMENTS

FR    1080718    12/1954

OTHER PUBLICATIONS

"Robot Claw Grabber" by Toysmith, Feb. 27, 2005, [retrieved on Aug. 16, 2013], 3 pages. Retrieved from: http://web.archive.org/web/20050227054600/http://www.toys2wish4.com/robclawgrab.html.

(Continued)

*Primary Examiner* — Dean Kramer
(74) *Attorney, Agent, or Firm* — Sheridan Ross P.C.

(57) ABSTRACT

A hand-held remote access device, such as a netting tool, includes a jaw portion having a pair of nets movable relative to each other between fully clamped and fully opened positions thereof, a handle portion spaced apart from the jaw portion by a bendable central portion that has a hollow, corrugated member having alternating ridges and grooves that is bendable so as to attain a predetermined shape.

20 Claims, 10 Drawing Sheets

(56) References Cited

U.S. PATENT DOCUMENTS

| | | | |
|---|---|---|---|
| 944,214 | A | 12/1909 | Rydquist |
| 1,051,374 | A | 1/1913 | Agin |
| 1,519,938 | A | 12/1924 | Smith |
| 1,957,944 | A * | 5/1934 | Dexter ............................ 43/12 |
| 2,613,100 | A | 10/1952 | Casey |
| 2,616,741 | A | 11/1952 | Ziese |
| 2,947,564 | A | 8/1960 | Winther |
| 3,219,376 | A | 11/1965 | Peters |
| 3,266,059 | A | 8/1966 | Stelle |
| 3,328,066 | A | 6/1967 | Johnston |
| 3,346,293 | A | 10/1967 | Wilcox |
| 3,527,492 | A | 9/1970 | Hollis |
| 3,576,343 | A | 4/1971 | Juhlin et al. |
| 3,617,084 | A | 11/1971 | Mares |
| 3,761,121 | A | 9/1973 | Reid |
| 3,901,545 | A | 8/1975 | Shott |
| 3,912,316 | A | 10/1975 | Veech |
| 3,934,915 | A | 1/1976 | Humpa |
| 4,033,618 | A | 7/1977 | Lamb |
| 4,039,216 | A | 8/1977 | Soos |
| 4,179,145 | A | 12/1979 | Shinsako |
| 4,186,955 | A | 2/1980 | Campbell |
| 4,225,174 | A | 9/1980 | Hennessy et al. |
| 4,248,468 | A | 2/1981 | Hastings |
| 4,253,697 | A | 3/1981 | Acosta |
| 4,272,116 | A | 6/1981 | Tufte, Jr. |
| 4,374,600 | A | 2/1983 | van Zelm |
| 4,393,728 | A | 7/1983 | Larson et al. |
| 4,398,759 | A | 8/1983 | Manola |
| 4,483,562 | A | 11/1984 | Schoolman |
| 4,501,230 | A | 2/1985 | Talo |
| 4,613,179 | A | 9/1986 | van Zelm |
| 4,647,094 | A | 3/1987 | Bergkvist et al. |
| 4,669,769 | A | 6/1987 | Polder, Jr. |
| 4,709,839 | A | 12/1987 | Tucker |
| 4,758,035 | A | 7/1988 | Shimasaki |
| 4,863,204 | A | 9/1989 | Peters |
| 4,865,371 | A | 9/1989 | Egberg |
| 4,878,703 | A | 11/1989 | Yoshioka |
| 4,962,957 | A | 10/1990 | Traber |
| 5,154,465 | A | 10/1992 | Pakosh |
| 5,380,054 | A | 1/1995 | Galvis |
| 5,503,442 | A | 4/1996 | Lee |
| 5,540,470 | A | 7/1996 | Lu |
| 5,572,913 | A | 11/1996 | Nasiell |
| 5,577,785 | A | 11/1996 | Traber et al. |
| 5,590,923 | A | 1/1997 | Berger et al. |
| 5,601,321 | A | 2/1997 | Simon |
| 5,601,322 | A * | 2/1997 | Forest ............................ 294/3 |
| 5,628,537 | A | 5/1997 | Kiemer |
| 5,647,622 | A | 7/1997 | Schectman |
| 5,667,146 | A | 9/1997 | Pimentel et al. |
| 5,707,303 | A | 1/1998 | Berkowitz et al. |
| 5,766,196 | A | 6/1998 | Griffiths |
| 5,778,939 | A | 7/1998 | Hok-Yin |
| 5,822,908 | A | 10/1998 | Blanchard |
| 5,823,592 | A | 10/1998 | Kalidindi |
| 5,857,723 | A | 1/1999 | Mathieu et al. |
| 5,895,082 | A | 4/1999 | Kaluzny |
| 6,042,155 | A | 3/2000 | Lockwood |
| 6,062,618 | A | 5/2000 | Figueroa |
| 6,148,773 | A | 11/2000 | Bogdahn |
| D439,402 | S | 3/2001 | Johnson |
| 6,257,634 | B1 | 7/2001 | Wei |
| 6,457,761 | B1 | 10/2002 | Benoit |
| 6,508,496 | B1 | 1/2003 | Huang |
| 6,513,844 | B1 | 2/2003 | Hsu |
| 6,520,556 | B1 | 2/2003 | Hsu |
| 6,571,479 | B1 | 6/2003 | Wu |
| 6,648,261 | B2 | 11/2003 | Irving |
| 6,669,254 | B2 | 12/2003 | Thom et al. |
| 6,739,637 | B2 | 5/2004 | Hsu |
| 6,796,587 | B2 | 9/2004 | Tsou |
| 6,845,736 | B1 | 1/2005 | Anderson |
| 6,848,731 | B2 | 2/2005 | Khubani et al. |
| 6,874,833 | B2 | 4/2005 | Keith et al. |
| 6,971,695 | B2 | 12/2005 | Backstrom |
| 7,004,520 | B2 | 2/2006 | Khubani et al. |
| 7,093,869 | B2 | 8/2006 | Jung |
| 7,325,849 | B2 | 2/2008 | Jones |
| 7,338,434 | B1 | 3/2008 | Haarstad et al. |
| 7,344,171 | B1 | 3/2008 | McMullan |
| 7,448,659 | B1 | 11/2008 | Auseklis |
| D591,122 | S | 4/2009 | Buzby et al. |
| 7,533,906 | B2 | 5/2009 | Luettgen et al. |
| 7,665,782 | B2 | 2/2010 | Buzby et al. |
| 7,677,619 | B2 | 3/2010 | Hutchings et al. |
| 7,695,035 | B2 | 4/2010 | Sumner et al. |
| 7,744,136 | B2 | 6/2010 | Waltz |
| 7,854,738 | B2 | 12/2010 | Lee et al. |
| D632,069 | S | 2/2011 | Thiessens |
| 7,934,756 | B2 | 5/2011 | Kroeze |
| 7,980,609 | B2 | 7/2011 | Khubani |
| 7,992,907 | B1 | 8/2011 | DeJesus |
| 8,061,751 | B2 | 11/2011 | Hatcher |
| 8,091,936 | B1 | 1/2012 | Graziano |
| 8,449,007 | B2 | 5/2013 | Farmer |
| 8,528,850 | B2 | 9/2013 | Bogdahn |
| 8,529,379 | B1 | 9/2013 | Faircloth |
| 8,585,114 | B2 | 11/2013 | Kovarik et al. |
| 8,602,917 | B2 | 12/2013 | Bennett |
| 8,807,615 | B2 * | 8/2014 | Kovarik et al. ............... 294/209 |
| 8,833,817 | B2 * | 9/2014 | Kovarik et al. ............... 294/1.4 |
| 2003/0236549 | A1 | 12/2003 | Bonadio et al. |
| 2004/0236316 | A1 | 11/2004 | Danitz et al. |
| 2005/0057055 | A1 | 3/2005 | Deal |
| 2006/0206101 | A1 | 9/2006 | Lee |
| 2008/0115400 | A1 * | 5/2008 | Capio ............................ 43/11 |
| 2010/0021279 | A1 | 1/2010 | Buzby et al. |
| 2012/0060878 | A1 | 3/2012 | Thiessens |
| 2014/0047757 | A1 | 2/2014 | Miller et al. |
| 2014/0054912 | A1 | 2/2014 | Bustos |
| 2014/0062113 | A1 | 3/2014 | Kovarik et al. |
| 2014/0137811 | A1 | 5/2014 | Kovarik et al. |

OTHER PUBLICATIONS

International Search Report and Written Opinion for International (PCT) Patent Application No. PCT/US2013/054275 mailed Jan. 10, 2014, 10 pages.

Official Action for U.S. Appl. No. 13/771,813 mailed Jun. 14, 2013, 9 pages.

Official Action for U.S. Appl. No. 13/771,813 mailed Sep. 5, 2013, 9 pages.

Notice of Allowance for U.S. Appl. No. 13/771,813 mailed Sep. 20, 2013, 6 pages.

U.S. Appl. No. 29/462,798, filed Aug. 8, 2013, Kovarik et al.

Official Action for U.S. Appl. No. 14/078,830 mailed Mar. 17, 2014, 7 pages.

Notice of Allowance for U.S. Appl. No. 14/078,830 mailed Apr. 11, 2014, 5 pages.

\* cited by examiner

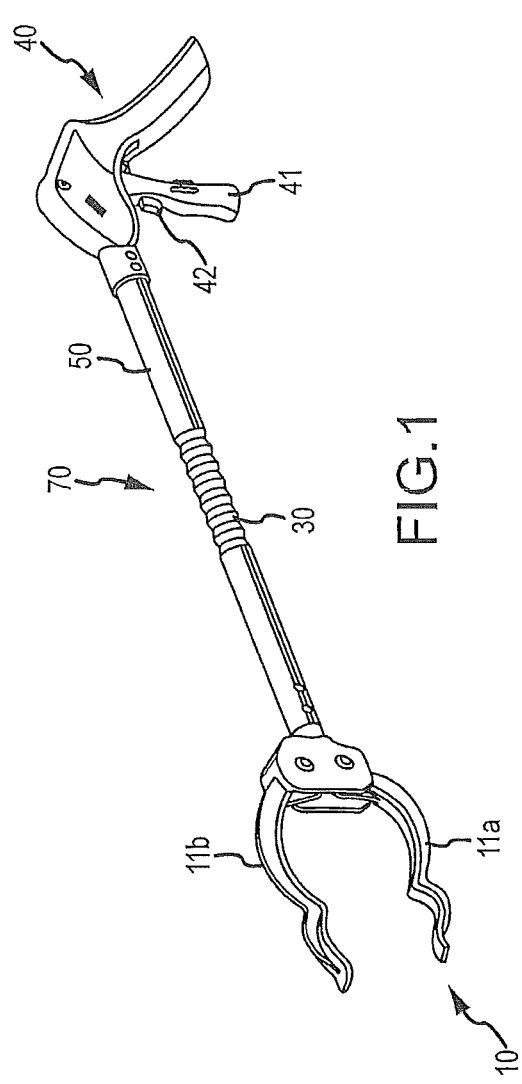
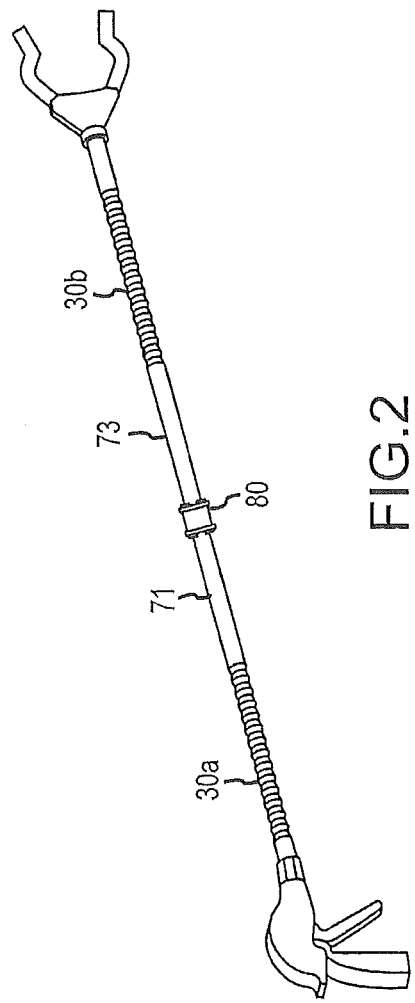

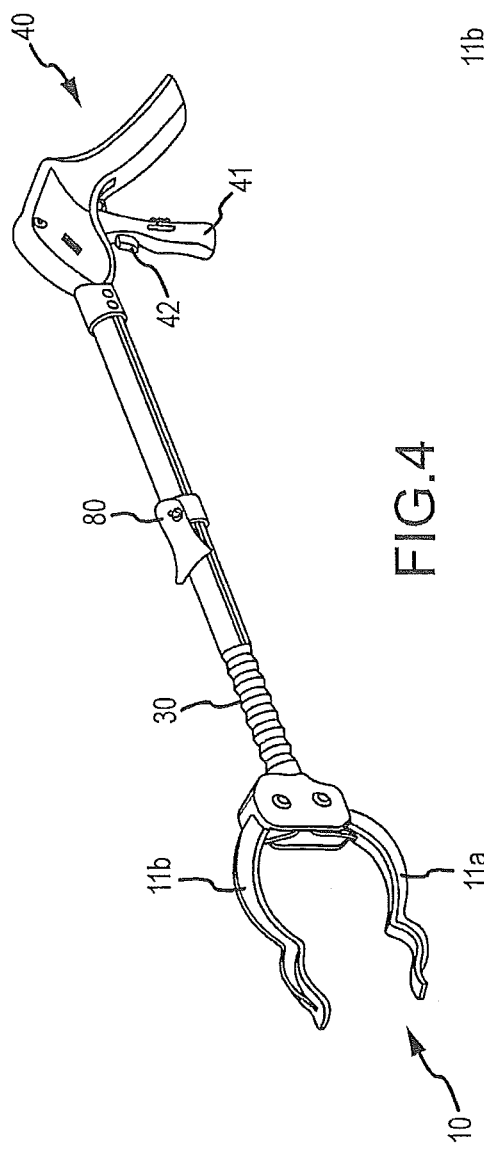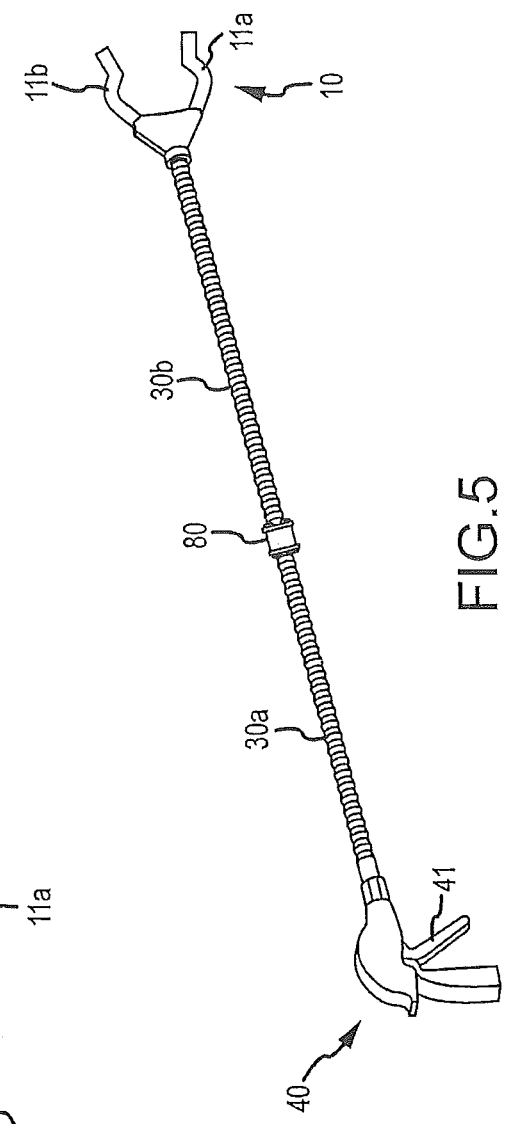

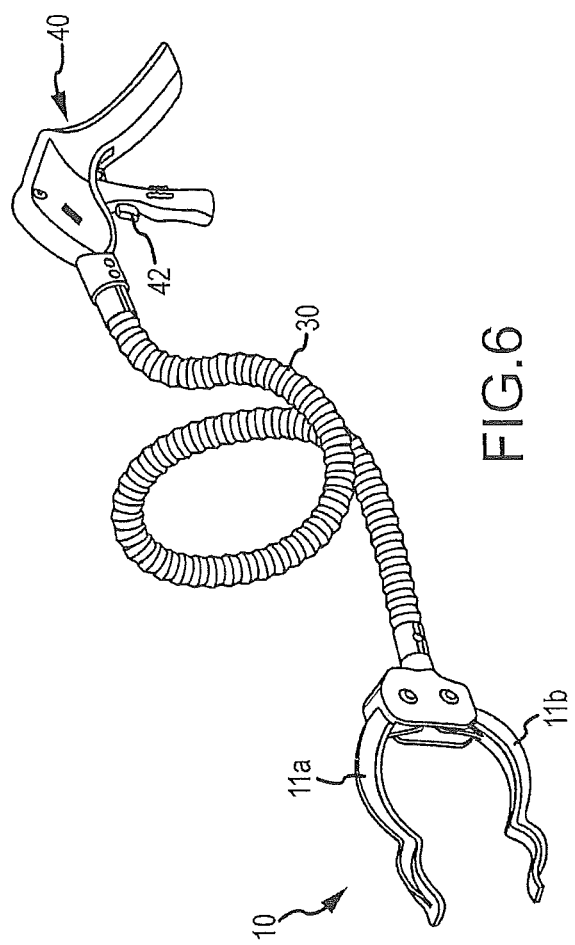

FISH NETTING TOOL

RELATED APPLICATIONS

This application is a continuation-in-part application of U.S. patent application Ser. No. 14/163,521 filed on Jan. 24, 2014, which is a continuation-in-part application of U.S. patent application Ser. No. 14/078,830 filed on Nov. 13, 2013, which is a continuation-in-part of U.S. patent application Ser. No. 13/771,813 filed on Feb. 20, 2013, now issued U.S. Pat. No. 8,585,114, and claims priority from U.S. Provisional Patent Application Ser. No. 61/601,789, filed on Feb. 22, 2012. This application also seeks priority from U.S. patent application Ser. No. 29/462,798, filed Aug. 8, 2013. The entire disclosure of the prior applications are considered to be part of the disclosure of the accompanying application and are hereby incorporated by reference.

FIELD OF THE INVENTION

The present invention is directed to a hand-held devices used for gripping objects or in achieving other remote functions, such device having at least one corrugated member that is bendable to position a remote end of such device into a desired orientation.

BACKGROUND OF THE INVENTION

Hand-held gripping devices for picking up and gripping objects have been known for years and typically employ a jaw portion and a handle portion spaced apart by a central portion. Such "grippers" typically have fixed-length central portions, although some have two part construction that permits a pivot point around the central portion of the device so that it can be stored more easily, and still others have telescoping portions to facilitate adjustable-length central portions.

There is a long felt but unsolved need for a remote access tool, such as a gripping device, that facilitates a user's ability to reach around corners or other angles that are not accessible via the use of traditional remote access tools that have non-bendable, straight central portions.

SUMMARY OF THE DISCLOSURE

The specification describes a hand-held gripping device, comprising a jaw portion having a pair of jaws movable relative to each other between fully clamped and fully opened positions thereof, and a handle portion spaced apart from the jaw portion by a central portion, which in some embodiments may be adjustable in length via telescoping portions slidingly moved to attain a desired length. The handle portion comprises a manually-actuatable trigger (although in other embodiments the activation of the trigger is via an electronic button) operatively connected to the jaw portion by a selectively extendible pull member at least substantially disposed within the central portion. Actuation of the trigger is operative to move the pull member to thereby selectively position the pair of jaws between the fully clamped and fully opened position thereof. The selectively extendible central portion may comprise a first tubular member and, if the device is adjustable with respect to its length, may employ rotatable locking members to reversibly lock the respective portions of the central column into a fixed position. In certain embodiments, the central portion comprises a hollow, corrugated member having alternating ridges and grooves, such member being bendable so as to attain a predetermined shape. Suitable material for use in the central column will be known by those of skill in the art, but, for example, hoses used for connecting gas appliances, such as coated, stainless steel gas connector hose is suitable for many embodiments as it reversibly bends via simple manual adjustment (or in certain embodiments, via a separate trigger element) into various desired directions and retains its bent position until further altered by the user. Alternative materials can be selected for various desired attributes, such as weight, cost, color, temperature characteristics, rigidity, corrosion resistance, electrical conductivity, water permeability, glow in the dark characteristics, etc. Thus, suitable connector material for use as the entire, or alternatively only a portion of the central portion of the gripping device, may comprise a hollow, corrugated member having alternating ridges and grooves, such member being bendable so as to attain a predetermined shape, and may be made of a variety of materials, including plastic, metal, and composites. The bendable portion of the central portion can be selectively or in a predetermined manner configured into a shape so as to facilitate easier access to a desired area, object, etc. The reversible nature of the bendable nature of the tool provides a user with the ability to adjust the angle of the distal portion of the tool to accommodate the myriad of difficult angles encountered by a user. Traditional remote access tools, which have straight and non-bending (as opposed to merely pivoting or telescoping) portions, are not able to achieve the desired remote access as provided by the present invention.

Extendable tools are typically used to interact with overhead objects that may be close or remote. For example, a fruit picker may be able to reach fruit; a janitor to replace light bulbs, and elderly person to grasp objects near their chair, tree pruners to reach certain limbs in particular orientations, etc. All of these various functions are made vastly easier by the provision of applicable forms of embodiments of the present invention as described in more detail (with respect to illustrative embodiments that one of skill in the art will appreciate transcend the particular field employed for illustrative purposes.)

In certain embodiments, at least one cord is employed that operatively connects the handle portion to the jaw portion, with such at least one cord extending through said central portion and through the hollow, corrugated member having alternating ridges and grooves. In certain embodiments, only the distal portion of the device has a segment of the hollow, corrugated member so as to limit the weight characteristics of such material as compared to the overall device. In certain embodiments, the hand-held gripping device has at least $\frac{2}{3}^{rd}$ of said central portion comprises said corrugated member. It has been found, however, that providing ten inches of such material is sufficient for many circumstances where a user desires to perform the desired bend to facilitate reaching an object to engage with the jaws of the device. As one will appreciate, however, any length of the hollow, corrugated member having alternating ridges and grooves can be used depending upon the circumstances. Thus, while in some embodiments, substantially the entire central portion comprises such material, in other embodiments, one or more sections of the central portion comprise such a hollow, corrugated member. In certain preferred embodiments, the distal portion has at least 1 inch of such hollow, corrugated member, more preferably at least about 3 inches of such material, and most preferably at least about 6 inches of such material. In other embodiments, at least two portions of the central column have sections with such hollow, corrugated member such that a user can preposition each section for a desired bent configuration, thus permitting the ability to reach an object remote form the user that may be difficult or impossible to reach using traditional gripper devices with straight central columns.

In certain embodiments, the hand-held gripping device employs a handle portion that has a second manually-actuatable trigger, with such second trigger able to adjust the orientation of the distally positioned jaw portion by effecting a change in the shape of the one or more corrugated members along the extent of the central portion. In some embodiments, the trigger that functions to alter the bending of the corrugated member is a rotatable knob, such that many varied angular orientations of the distal end (with the jaws) can be attained via rotation of a knob positioned near or on the hand grip of the device. Electronic means can also be employed for such purpose, as well as for the operation of the jaws between their closed and open positions.

While certain embodiments solely employ at least one section of a corrugated member to achieve desired bendable characteristics, other embodiments of the hand-held gripping device have a portion of said central portion that is in telescoping relationship with an adjacent portion of said central portion. Telescoping shafts may have two or more shaft members so long as each inner member is slightly smaller in cross-sectional area than the next outer member. In such embodiments, a locking member associated with said central portion is used to fix two adjacent members of said central portion in an engaged position, with the locking member operable between a first locking position and a second unlocking position. The locking member may comprise a coupling member, such as rotatable collar that can be manipulated by a user to adjust the griping member's length. In one embodiment, a section of corrugated hollow material is positioned at the distal end of the device, about 3 to 6 inches away from the jaws (and in the direction of the hand grip) and two adjacent members of the central column portion are operatively associated with each other in a slidingly telescoping relationship with a locking member is associated with at least one of said two adjacent members, the locking member comprising a selectively radially expandable mandrel radially expanded into engagement with the adjacent members to permit the length of the central column member to be varied.

In preferred embodiments, a pull member comprises first and second pull rods and a cam body supporting a cam is used, with the pull rods associated with the cam support body. The cam is characterized by a first, engaged condition in which the cam is in contact with the second pull rod to thereby fix the length of the pull member, and a second, disengaged condition in which the cam is out of contact with the second pull rod to thereby permit the length of the pull member to be varied. The user-actuatable trigger comprises a manually operable release trigger provided on the handle portion, which is, operatively connected to the cam via a connecting rod.

One of skill in the art, especially guided by the incorporated references, will appreciate the varied types and features of gripping devices that can be constructed and that further incorporate the hollow corrugated member(s) as described herein in order to attain desired bendable capabilities of a particular user. For example, and without limitation, the present invention can be employed in a variety of fields where the problem of access around otherwise difficult angular orientations is presented, such fields including but not limited to the following: fruit pickers; janitors replacing light bulbs, elderly persons grasp objects near their chair, tree pruners; surgeons and dentists/orthodontists to reach interior portions of a person's anatomy, etc.

While preferably the bendable portion of the central column is made of a corrugated material (due to its ability to remain open in its central internal core, thus permitting pull cords to operate therein), those of skill in the art will appreciate that—especially dependent upon how severe and desired bending may be—that other types of bendable segments can be employed to achieve such a function. For example, pliable plastic or rubber-type sections can also be alternatively or in conjunction employed on a gripper device of the present invention so as to achieve the ability of a user to reach objects that would be difficult or nearly impossible using a device having a straight and non-bendable column. Of course, the ability of such a section to uphold the weight of the jaws, especially after the jaws have grasped some desired object, is an important consideration when selecting appropriate materials to employ for the bendable portion of the column. In other words, a sufficient amount of rigidity and/or operational integrity of the central column is required for most applications.

In still other embodiments of the present invention, one or more springs can be employed (with such spring(s) having desired structural integrity with respect to an ability to bend, an ability to support weight that may be encountered when the jaws engage an object and the device is lifted in the air, etc). Thus, in one embodiment, a section of spring is used along the central portion of the device with a cord mechanism that is attached to the jaw end of the device, such that when the cord is pulled, the spring section bends to angularly adjust the jaws such that they can reach around corners otherwise inaccessible with a straight column gripper device.

To comply with appropriate written description and enablement requirements and to provide sufficient guidance in how one of skill in the art can make and use the various and numerous embodiments of the present invention, incorporated herein in their entireties are the following: Hsu, U.S. Pat. No. 6,513,844; U.S. Pat. No. 6,520,556, U.S. Pat. No. 6,739,637, and U.S. Pat. No. 4,669,769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 8,061,751 to Hatcher; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669,769; U.S. Pat. No. 6,257,634; U.S. Pat. No. 7,004,520; U.S. Pat. No. 6,513,844; U.S. Pat. No. 6,571,479; and U.S. Pat. No. 6,848,731.

Some extendable tools have fixed tool heads, e.g. a dust mop, or a flexible tool head, e.g. a device for swapping out light bulbs that has spring-like fingers. Other extendable tools include a hand powered actuatable tool head assembly having movable elements, such as, but not limited to, a tree pruner. In other embodiments, extendable tools have an actuatable tool head assembly that have drive assemblies in order to allow the user at the bottom end of the extendable tool to actuate the tool head at the upper end of the extendable tool. While an actuatable tool head assembly associated with one end of an extended tool may be any type of tool, and while the present discussion relates in particular to a tool having a jaw assembly as an example, more specifically a reaching tool that may be used to grip objects between the two jaws, it will be understood by those of skill in the art that various known tool head assemblies can supplant the discussion of clasping jaws and thus, will otherwise suffice to describe the novel and non-obvious aspects of the present invention in such other embodiments and functions.

Thus, as opposed to the prior art, where materials employed for the central column were hardened plastic polymers or any of substantially non-malleable metals, the present invention can be seen as distinctly different as it relates to employing materials and constructions that bend or otherwise flexible so as to achieve the functional attributes that the prior art devices cannot achieve.

Another aspect of the present invention is directed to a double headed fishnet which creates a trap or cage to allow the user to easily catch fish, especially in a fish tank, but in other embodiments, useful for sport fishermen, fish farming operations, etc.

Cleaning a fish tank often requires that the fish residing within be temporarily removed and stored in alternative tank while their primary fish tank is being cleaned. To catch and remove the fish from the fish tank, a wide range of fishnets designed specifically for that purpose have been developed and produced. These fishnets are also used in pet stores when a person purchases a new fish for their fish tank. The pet store worker must capture the often specifically chosen fish for the customer and secure that fish in a bag for transport to the customer's fish tank. This can be extremely difficult with a traditional one headed fishnet as fish can be particularly agile. Thus, one object of the present invention to provide an apparatus which facilitates the swift and easy capturing of fish in a fish tank. In some embodiments, the present invention utilizes a dual headed design that is capable of opening and closing. In other embodiments, a side skirt net is used to close off three sides of the net end of the apparatus in addition to the two sides of the dual net heads. This configuration makes sure that only one side (the front) of the six sided net end is open, closing off any route of escape for the fish, making it very easy for a user to catch fish by simply lowering the net end directly down around the fish and closing the apparatus, allowing easy removal of the fish from the tank.

Generally is not desirable for users to touch the fish with their hands when the fish are transferred, such as when the tanks are cleaned. With at least some known fish nets, depending on the size, strength, and/or activity level of the fish, for example, a risk exists that a fish may leap, wriggle, or otherwise escape from the net as it is being transferred from one aquarium to another. Depending on the size, speed, and/or activity level of the fish, capturing a fish in such a net may be a time-consuming and/or difficult task. Thus, in one embodiment, net assemblies are moveable from a closed position wherein the first net assembly is positioned in contact against the second net assembly, to an open position wherein the first net assembly is positioned a distance away from the second net assembly.

Using the present aquarium tool, a user can safely and quickly transfer fish from one location to another with a single hand and in such a manner that the risks of the netted fish undesirably exiting the net are reduced in comparison to known fish nets. More specifically, the fish net includes a pair of net assemblies. The frames of each net assembly are configured to contact in a mating relationship when the jaw portion is moved to the closed position. The mating relationship of the frames substantially prevents the netted fish from exiting the fish net. As a result, a fish net is provided which facilitates reducing the risk of a netted fish from inadvertently escaping the captivity of the fish net in a cost-effective and reliable manner. In one embodiment of the present invention, the jaw portion of the flexible reacher is adapted to provide at least one fish net assembly such that at least one, but preferably both of the movable jaws is designed so as to have a net associated therewith, preferably where each net assembly has a rim which reversibly contacts an opposing net assembly (when the trigger is operated). This achieves a net closing function, e.g. such that fish can be encompassed within the movable jaws of opposing net material, enabling a person attempting to catch/net a fish in an enclosure, such as an aquarium. One can position the opposing net structures in a region where the desired fish is located, whereby the operation of the trigger causes the two opposed nets to move closer together into a fully closed position, which co-aligns the outer rim portions of opposing nets, thus providing a way to encircle and trap a fish in a net without having to move (as is traditionally done) a single net structure to the surface to entrap the fish.

The ability to pre-bend the aquarium fish net tool provides one who wishes to net a particular fish with the ability to approach a fish in a typical tight hiding place inside an aquarium, where fish reside when scared or wary. Thus, when a desired fish moves to a presumably safe place under a rock cliff of an aquarium or in a fashioned underwater cave—using the present invention one can place the opposed fish net in position in the cave or under the cliff, where the fish is likely to move once startled—thus providing a far quicker way in which to net such fish.

Also incorporated by reference in its entirety are US Pat. Publication No. 20140047757 to Miller, and U.S. Pat. No. 5,822,908 to Blancard, which are generally directed to types of suitable fish net structures that may be employed in the manufacture and use of the various embodiments of the present invention, as well as U.S. Pat. Publication no. 20140054912 to Bustos and U.S. Pat. No. 7,677,619 to Hutchings for particular features, such as inclusion of lights, magnets, etc. in conjunction with the claimed device.

BRIEF DESCRIPTION OF THE DRAWINGS

Other advantages of the present invention will be readily appreciated as the same becomes better understood by reference to the following detailed description when considered with the accompanying drawings, wherein:

FIG. 1 is a lateral perspective view of an extendible gripping device according to the present invention;

FIG. 2 is another view of one embodiment showing the corrugated section(s) of the central column near the jaw portion of the inventive gripping device and toward the handle portion of the device.

FIG. 4 is a perspective view showing another embodiment with a corrugated segment in addition to a telescoping locking member along the central column.

FIG. 5, shows a perspective view of an embodiment where substantially the entire length of the central column comprises a corrugated segment.

FIG. 6 shows how the corrugated segment can be bent into configurations, including winding the central column around so that the device can be stored and transported easily.

WRITTEN DESCRIPTION OF A CERTAIN PREFERRED EMBODIMENT

Figure 3:
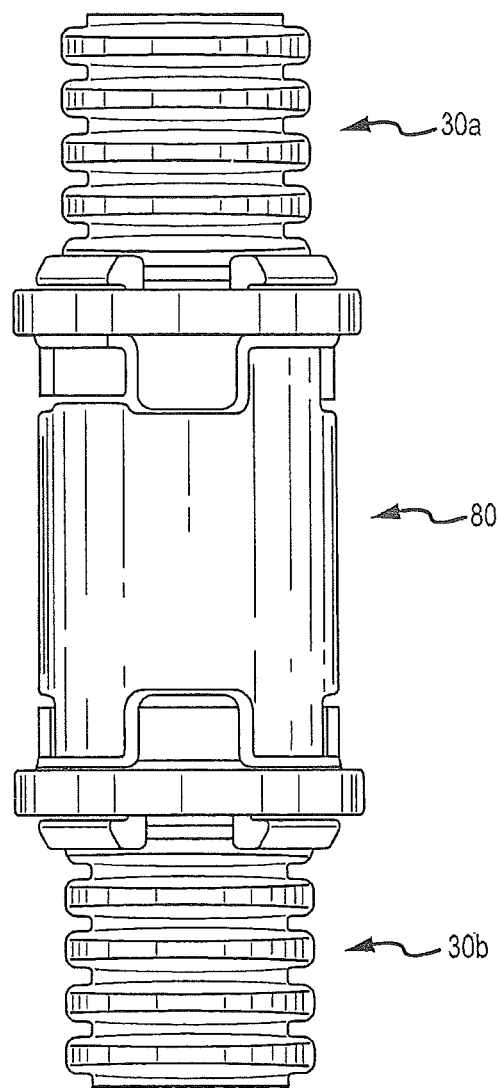
FIG. 3 comprises a perspective close-up view of one embodiment of a corrugated section of the column, showing a dissociable coupling.
Figure 7:
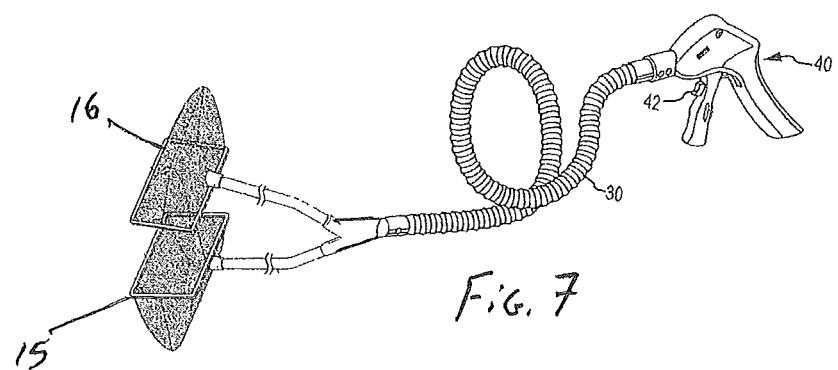
FIG. 7 shows a perspective view of an embodiment where a jaw portion comprises a net assembly comprising a pair of nets that are movable relative to each other between fully clamped and fully open positions.
Figure 8:
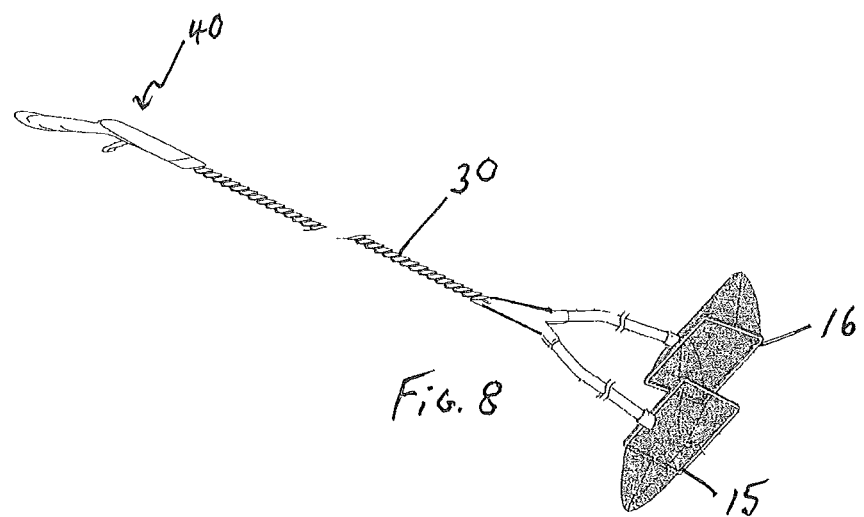
FIG. 8 shows a perspective view of a further embodiment of a net assembly where the flexible portion between a handle and such assembly is variable in length.
Figure 9:
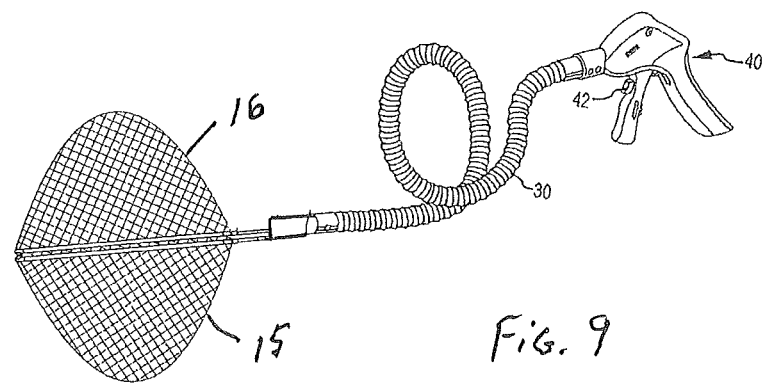
FIG. 9 shows a perspective view of another embodiment where the pair of nets is in a closed position.

It will be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention. For the following description, the actuatable tool head assembly is described as a gripper having a jaw assembly). It is understood, however, that any type of actuatable tool head assembly may be used.

As disclosed in the figures, various embodiments of the present invention generally comprise a hand-held gripping device having a jaw portion (indicated generally at 10) comprising a pair of jaws 11a, 11b and a handle portion (indicated generally at 40) spaced apart by a selectively extendible central portion (indicated generally at 70). The handle portion 40 comprises a manually-actuatable trigger 41 operatively connected to the jaws of the jaw portion by a pull member. Actuation of the trigger 41 is operative to move the pull member to thereby selectively position the pair of jaws 11a, 11b between fully clamped and fully opened positions thereof. It will be understood that the jaw construction and the handle portion construction is intended as exemplary only, and that those of skill in the art will appreciate how to adapt such portions as desired, consistent only with facilitating operation of the bendable column gripping device as hereinafter described.

A pull member is interconnected with the jaw and handle portions such that manual actuation of the trigger 41 effects movement of the jaws 11a, 11b.

In certain embodiments, the user-actuatable release trigger of the present invention comprises a release button 42 disposed on the trigger 41 of the handle portion 140. In the event that the distance between the jaw portion and the handle portion is not appropriate in light of the task contemplated by the user, the user may adjust the length of the central portion by first unscrewing a collet assembly to thus permit telescoping movement of first and second tubular members. The user next actuates the release trigger, either by depressing the release button or turning the collar (depending on the form of the invention), which actions cause the second coupling to move from the engaged to the disengaged position. At this point, the pull member may be lengthened or shortened concurrently with telescoping movement of the first and second tubular members. Thus, while depressing the release trigger, the user grasps the second tubular member and changes the distance between the handle portion and the gripping portion as desired. After the desired length is obtained, the user releases release trigger and tightens the collet assembly to thereby fix the lengths of each of the central portion and the pull member.

Selective positioning of the first and second tubular members may be effected by rotational movement of one of the first or second tubular members of the central portion.

In certain embodiments, the gripping device of this embodiment comprises a selectively extendible central portion 70 including a first tubular member 71 slidingly telescopingly received within a second, larger-diameter tubular member 73. In order to fix the relative positions of the first 71 and second 73 tubular members, there is provided a collet assembly 80.

A locking mechanism may be provided to fix the pivotal position of the trigger 41, and thereby fix the relative positions of the jaws between the fully open and fully closed positions thereof.

In operation, from the position wherein the jaws are fully opened, a user manually depresses trigger 41 to retract the pull rod 50 and thereby move the jaws toward each other.

To understand and appreciate the varied and numerous applications of the present invention in the context of tools that do not employ the gripping jaw device used as an illustrative example herein, the inventors incorporate by reference herein, in their entireties, the following patents to provide the detailed embodiments that, with the features here described, facilitate far easier access to previously difficult to reach areas so that the various functional assemblies at the remote end of a tool can be used effectively: Hsu, U.S. Pat. No. 6,513,844, U.S. Pat. No. 6,520,556, and U.S. Pat. Nos. 6,739,637, 4,669, 769 to Polder, Jr; U.S. Pat. No. 4,962,957 to Traber; U.S. Pat. No. 8,061,751 to Hatcher; U.S. Pat. No. 7,934,756 to Kroeze; U.S. Pat. No. 8,061,751 to Hatcher; U.S. Pat. No. 7,665,782 to Buzby et al.; U.S. Pat. No. 8,091,936 to Graziano; U.S. Pat. No. 7,980,609 to Khubani; U.S. Pat. No. 5,895,082 to Kaluzny; U.S. Pat. No. 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669, 769; U.S. Pat. No. 6,257,634; U.S. Pat. No. 7,004,520; U.S. Pat. No. 6,513,844; U.S. Pat. No. 6,571,479; and U.S. Pat. No. 6,848,731.

It will be appreciated from the above disclosure that the present invention improves upon the prior art by providing a bendable gripping device that is robust yet simple in design, and that allows easy adjustment of the direction of the jaws to reach around tight corners or other places where a straight columned device would simply not function to retrieve desired objects remote form the user.

In one embodiment, a hand held gripping device is provided that has a jaw portion comprising a pair of jaws that are movable relative to each other between fully clamped and fully open positions. A handle portion is spaced apart from the jaw portion by a selectively extendable portion, the handle portion having a manually actuable trigger connected to the jaw portion. An extendable pole member, preferably running longitudinally through a tubular section, operatively connecting the jaw portion to the handle portion, is provided. Actuation of the trigger is therefore operative to move the pole member to selectively position the pair of jaws between fully clamped and fully opened positions. Between the jaw portion and the handle portion is therefore a central portion, preferably comprising a hollow, corrugated member 30. Such corrugated member 30 preferably has alternating ridges and grooves such that the central portion of the device is able to bend in order to attain predetermined shapes. In particular embodiments, at least one cord is connected between the handle portion and the jaw portion, such that the cord extends through the central portion of the device.

As illustrated in FIG. 2, in certain embodiments of the present invention, two or more corrugated members 30a and 30b are provided at different relative locations along the device, and more specifically along the central portion of the device. In preferred embodiments, at least two thirds of the central portion comprises the corrugated member 30. In still other embodiments, at least a central portion of the device is in a telescoping relationship with an adjacent portion of the device, namely, a first portion 71 is telescopically related to a second portion 73, with a locking member, preferably a locking collar, associated with a central portion. The locking member 80 is provided in a fashion so that the two adjacent members of the central portion 71, 73 may be in an engaged position such that the length of the central portion 70 can be effectively adjusted by the user. The locking member 80 can alternatively be referred to as a coupling member between the two portions 71 and 73. In a preferred embodiment, the locking member comprises a selectively radially expandable mandrel.

In other embodiments, a user actuable trigger comprises two operable triggers with the operation of a first trigger causes the reversal opening and closing of the jaws, whereas the other trigger causes the distal end of the device to move such that the distal end bends in relationship to the longitudinal axis of the device.

In other embodiments, a selective positioning of a knob, such knob position near the trigger/handle portion of the device, is provided in order to cause rotational movement of the distal end of the device through manual adjustment of the knob.

Figure 10:
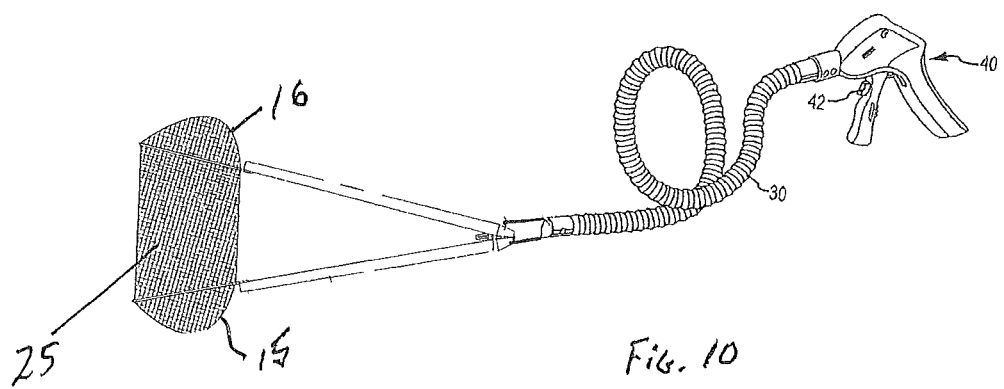
FIG. 10 shows a perspective view of a further embodiment where the net assembly is a five-sided net and the net assembly is in an open position.
Figure 11:
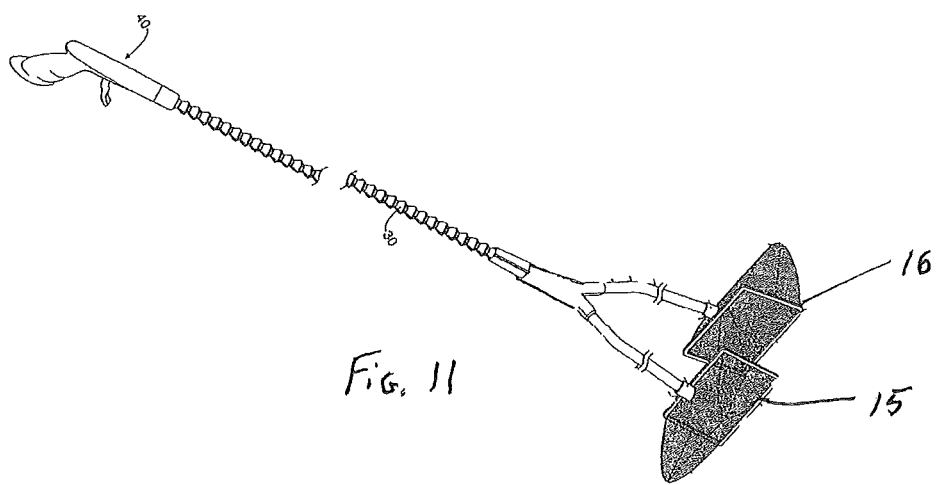
FIG. 11 shows a perspective view of one embodiment where the net assembly is connected to a plurality of interconnected connectors.
Figure 12:
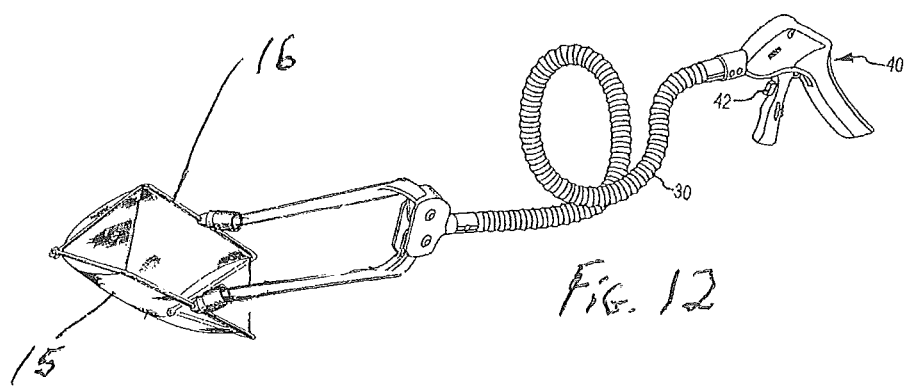
FIG. 12 shows a perspective view of an embodiment where the net assembly has an open side of the net assembly facing the jaw portion.

In still other embodiments (for example, FIG. 5) the majority of the portion between the handle portion and the jaw portion comprises corrugated material 30. In such an embodiment, a locking member 80 can be employed, so as to selectively adjust the length of the device in a telescoping relationship, even though the telescoping members themselves are made of a corrugated, bendable material. In other embodiments, however, the locking member 80 can be dispensed with, and the corrugated member 30 can comprise the entirety of the portion between the handle portion and the jaw portion of the device. In such embodiments, it is possible to compress the device in a coiled manner, making transportation and storage of such a device far easier. For example, the bendable nature of the corrugated members used with the device can be employed in order to compact the device to fit within luggage, purses, etc., that may be carried by individuals, especially elderly individuals in need of such a compact, adjustable device. As can be seen in FIGS. 7-12, various fishing net assemblies, ranging in shape, design, materials, dimensions, and orientation with respect to the central column, etc. can be employed. Thus, one aspect of the present invention has particular application for aquarium owners, scuba divers, snorkelers, and fishermen. The bendable nature of the device as described herein makes it particularly portable, and easily carried by those on a boat, in a scuba/snorkeling bag or stowed near an aquarium for accessible use. The hand-held fish netting tool is preferably adapted to permit reversibly disassociable net attachments such that different types, designs, sizes, mesh patterns, geometries, etc. can be accommodated by a user's selection of desired nets for particular uses. For example, a user may fit the device with a small net pair to facilitate capturing fish in an aquarium, while selecting a much larger set of nets for a boat fishing experience. The various ways the net pairs can be reversibly attached will be readily appreciated by those skilled in the art, but one preferred way is to fashion the distal end of the device with a fitted connector that can be pulled outward via a spring attachment associated with the cord extending through the device. A mating hook structure may be employed to attach associated net pairs to the bendable tool at such distal end. For example, FIG. 10 shows one embodiment of the present invention that provides a double-headed fishing net that allows a user to more efficiently and effectively swift through a fishing tank and capture a fish. A first net head 15 and a second net head 16 allow the present invention to surround a fish from two opposing sides. In other embodiments, a lateral net is used to surround the fish from three additional sides. Consequently, the first net head 15, the second net head 16, and the lateral net 25 are used to form a five-sided fishing net, which allows a user to more easily capture a fish by enclosing the fish on five different sides. The first net head 15 and the second net head 16 are pressed against each other to prevent the fish from escaping. Different kinds and sizes of net heads may be attached to allow for a wide range of different configurations. Indeed, in some embodiments, only one net is employed on one side, with the other clamping/closure member being a more rigid net/mesh materials (similar to a tennis racket surface) so that the fish is trapped when the jaws close together, forcing the fish into the looser net side of the clamped structure. Thus, in one embodiment the tool comprises a pair of net assemblies where one of the pair is a rectangular shaped wire structure with a loose net associated therewith, and the opposing paired structure is a rectangular shaped wire structure with a taut net associated therewith.

While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

What is claimed is:

1. A hand-held fish netting tool comprising:
a jaw portion comprising a pair of net assemblies having a frame and a net coupled to said frame, said net assemblies movable relative to each other between fully clamped and fully opened positions thereof; a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of net assemblies between the fully clamped and fully opened position thereof; wherein the central portion comprises at least two separate portions comprising hollow, corrugated members that have alternating ridges and grooves, said central portion being bendable so as to attain a predetermined shape so that a user can preposition said tool into a desired bent configuration; and said pull member comprising at least one cord operatively connecting the handle portion to the jaw portion, said at least one cord extending through said central portion.

2. The tool as set forth in claim 1, wherein said frame comprises a substantially rectangularly shaped frame.

3. The tool as set forth in claim 1, wherein said net assemblies are substantially concentrically aligned when said net assemblies are in said clamped position.

4. The tool as set forth in claim 1, wherein at least one of said net assemblies is removably coupled to said jaw portion.

5. The tool as set forth in claim 1, wherein at least a portion of said central portion is in telescoping relationship with an adjacent portion of said central portion.

6. The tool as set forth in claim 1, further comprising a locking member associated with said central portion to fix two adjacent members of said central portion in an engaged position, said locking member operable between a first locking position and a second unlocking position.

7. The tool as set forth in claim 1, wherein the actuatable trigger comprises a manually operable release trigger.

8. The tool as set forth in claim 1, wherein the central portion comprises glow in the dark material.

9. The tool as set forth in claim 1, wherein said pair of net assemblies consist essentially of a first loose net portion associated with a rectangular shaped wire structure and an opposing taut net portion associated with a rectangular shaped wire structure.

10. A hand-held fish netting tool comprising:
a jaw portion comprising a pair of net assemblies having a frame and a net coupled to said frame, said net assemblies movable relative to each other between fully clamped and fully opened positions thereof; a handle portion spaced apart from the jaw portion by a selectively extendible central portion, the handle portion comprising a first actuatable trigger operatively connected to the jaw portion by a selectively extendible pull member at least substantially disposed within the central portion, whereby actuation of the trigger is operative to move the pull member to thereby selectively position the pair of net assemblies between the fully clamped and fully opened position thereof; wherein the central portion comprises at least two separate portions comprising hollow, corrugated members that have alternating ridges and grooves, said central portion being bendable so that a user can position said tool into a desired bent configuration; and said pull member comprising at least one cord operatively connecting the handle portion to the jaw portion, said at least one cord extending through said central portion;
wherein at least one of said net assemblies is removably coupled to said jaw portion; and
wherein the actuatable trigger comprises a manually operable release trigger.

11. The tool as set forth in claim 10, wherein said frame comprises a substantially rectangularly shaped frame.

12. The tool as set forth in claim 10, wherein said net assemblies are substantially concentrically aligned when said net assemblies are in said clamped position.

13. The tool as set forth in claim 10, wherein at least a portion of said central portion is in telescoping relationship with an adjacent portion of said central portion.

14. The tool as set forth in claim 10, further comprising a locking member associated with said central portion to fix two adjacent members of said central portion in an engaged position, said locking member operable between a first locking position and a second unlocking position.

15. The tool as set forth in claim 10, wherein the central portion comprises glow in the dark material.

16. The tool as set forth in claim 10, wherein said pair of net assemblies consist essentially of a first loose net portion associated with a shaped wire structure and an opposing taut net portion associated with a shaped wire structure.

17. A hand-held fish netting tool comprising: a jaw portion comprising a pair of net assemblies having a frame and a net coupled to said frame, said net assemblies movable relative to each other between clamped and opened positions thereof; a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of net assemblies between the clamped and opened positions thereof; wherein the central portion comprises at least two separate portions comprising hollow, corrugated members that have alternating ridges and grooves, said central portion being bendable; and said pull member comprising at least one cord operatively connecting the handle portion to the jaw portion, said at least one cord extending through said central portion, and wherein a coupling member is between said at least two separate portions.

18. The hand-held fish netting tool of claim 17, wherein said pair of net assemblies are reversibly disassociable to accommodate different types, designs, sizes, mesh patterns, and geometries of net attachments.

19. The hand-held fish netting tool of claim 17, wherein said pair of net assemblies form a five-sided net.

20. The hand-held fish netting tool of claim 17, wherein said pair of net assemblies comprises one structure with a loose net and an opposing paired structure with a taut net.

* * * * *